United States Patent [19]
Williams

[11] Patent Number: 5,636,379
[45] Date of Patent: Jun. 10, 1997

[54] JAW-JOINT PROTECTIVE DEVICE

[76] Inventor: Edward D. Williams, 1432 Washington La., Philadephia, Pa. 19138

[21] Appl. No.: 511,698

[22] Filed: Aug. 4, 1995

[51] Int. Cl.$^6$ .................. A41D 13/00; A61C 5/14
[52] U.S. Cl. .................................. 2/455; 128/862
[58] Field of Search .............. 2/2, 9, 424; 128/859, 128/861, 862, 848; 433/6; 602/5, 6, 17

[56] References Cited

U.S. PATENT DOCUMENTS

| | | | |
|---|---|---|---|
| 2,483,157 | 9/1949 | Singer | 128/861 |
| 2,521,039 | 9/1950 | Carpenter | 128/861 |
| 2,966,908 | 1/1961 | Cathcart et al. | 128/861 |
| 3,126,002 | 3/1964 | Owens | 128/861 |
| 4,568,280 | 2/1986 | Ahlin . | |
| 4,810,192 | 3/1989 | Williams . | |
| 4,955,393 | 9/1990 | Adell | 128/861 X |
| 5,092,346 | 3/1992 | Hays et al. | 128/861 X |
| 5,117,816 | 6/1992 | Shapiro et al. | 128/861 X |
| 5,277,202 | 1/1994 | Hays | 128/861 X |
| 5,447,168 | 9/1995 | Bancroft | 128/861 X |

*Primary Examiner*—Paul C. Lewis
*Attorney, Agent, or Firm*—David Edwards

[57] ABSTRACT

A jaw joint protective device is provided for protecting teeth, lips, jaw, and other delicate structures of the vital cranial triad (VCT) from injury and/or for supporting the condyle of the temporomamdibular joint (TMJ) in a relatively fixed (stable) position thereby stabilizing the jaw and the VCT during head contact activity and or permit the components of a VCT disorder to be realigned for proper healing. This device is an over-the counter purchased, boil and bite jaw-joint protector providing maxillary and mandibular teeth seats for protection of the mouth and/or healing of the VCT. This invention provides for customized over-the counter availability that adds speech and airway capabilities to the device to facilitate sports participation.

9 Claims, 1 Drawing Sheet

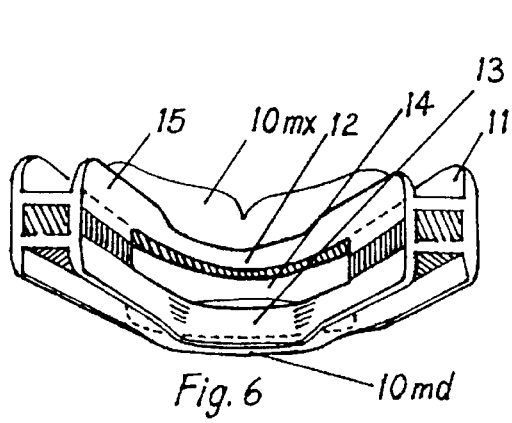
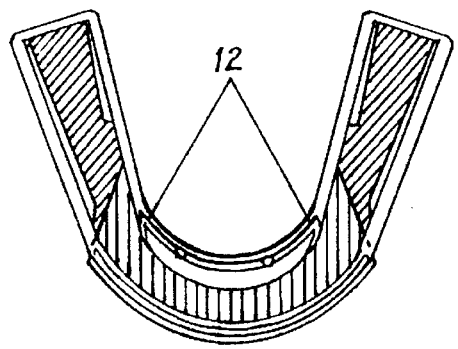
Fig. 6
Fig. 5
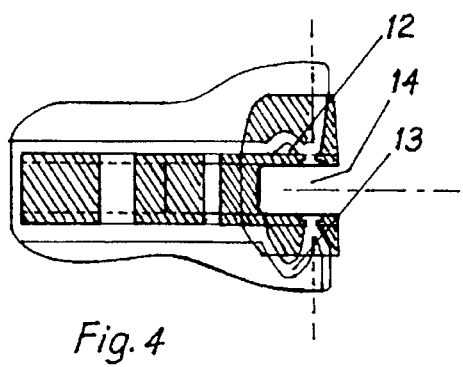
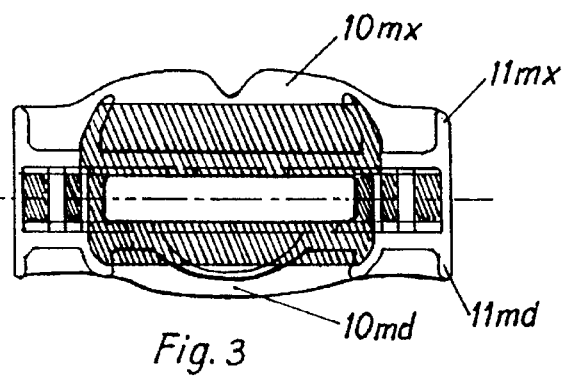
Fig. 4
Fig. 3
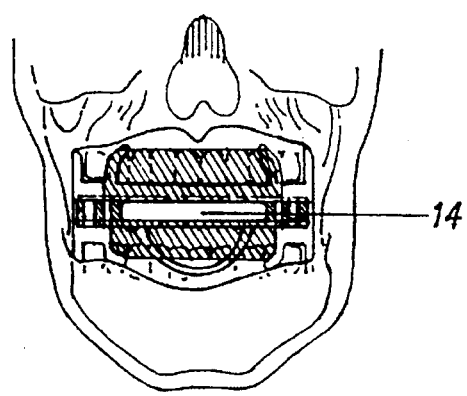
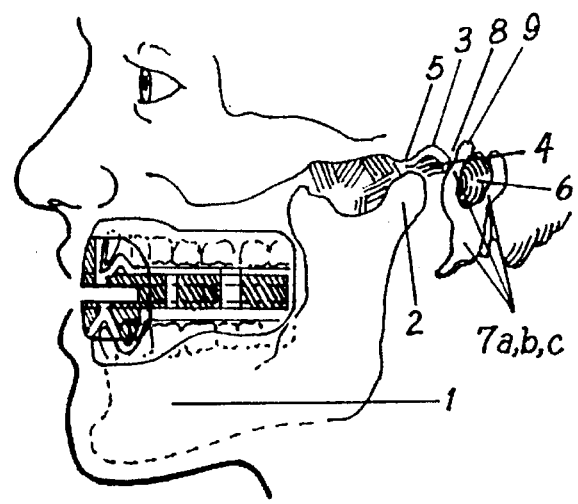
Fig. 2
Fig. 1

JAW-JOINT PROTECTIVE DEVICE

This invention relates to a jaw-joint protector for protecting teeth, lips, jaw joint, and other delicate structures of the head including the vital cranial triad (VCT), which is comprised of the bones and tissue structures found in the temporomandibular joint (TMJ), the temporal tympanic bones of the ear, and the inferior surface of the petrous temporal bones, from injury during sports and head contact conditions.

Prior to the present invention, disorders, to the VCT have been overlooked, ignored, and misdiagnosed. Although many rules, regulations and equipment in contact sports such as football, boxing, hockey, soccer and contact karate exist for protecting the body, the VCT of the head still needs adequate protection. The use of the common mouth guard has reduced the incidence of dental injuries. However, in general, the design of the mouthguard has increased the incidence of injury and load forces to the delicate jaw joint and component structres of the VCT. Although a high percentage of contact sport athletes have a VCT disorder, the symptoms are often ignored and not associated with jaw-joint injuries. It has been estimated that these disorders are more widespread with up to 50% of the population seeking dental treatment exhibiting some degree of VCT dysfunction. The trauma produced in this joint has greater effects and manifestations than trauma produced in any other joint of the body and the symptoms will affect the participant long after the games are over. The trauma produced in this joint during sports conditions has not come under the close scrutiny and has been largely ignored by health, sports and governmental organizations. The seriousness of the injury to the VCT is due mainly to its anatomical structure, its functions, and its approximation to the cerebral housing. The participants, such as boxers, being the most proficiently trained in the administration of trauma to this delicate area, have created crippling injuries beyond imagination. The Health Profession must begin to focus its attention to treatment, care, maintenance, and prevention of injury to this VCT.

VCT dysfunctions are pathologic conditions of the craniomandibular articulation which affect mandibular opening, mastication, deglutition, and possibly other neurologic functions. Common types of dysfunction are internal derangement and structural fractures. They can be caused by a blow to the head, chin, or jaw due to a contact sport, an accident, attacks of violence, or just a simple fall. Stress, strain, tension, environmental pressure, and noise can also cause dysfunction of the VCT. The premature loss of teeth, especially the molar teeth, can cause disorders. These dysfunctions can be caused in infants by compression of the VCT area at the time of child birth; this normally occurs by misuse of forceps by a doctor when pulling an infant down the birth canal of the mother.

Internal derangement of the VCT may manifest itself in many symptoms, for example: pain around the neck, eyes, and ears, popping or clicking of the disc within the VCT; clinching of facial muscles; grinding of teeth; malocclusion (i.e., teeth do not meet together well or meet improperly); ringing in the ears; noticeable rapid fatigue during physical activities; increased irritability; headaches of unknown origin; and the decrease of one's physical output or loss of strength not realized by the participant.

One of the effects of the VCT dysfunction is that the biting muscles of the jaw become sore, which may cause other debilitating dysfunctions. If VCT dysfunctions are not treated early, damage is often irreversible.

Many methods of treatment exist for correcting TMJ dysfunction. One method of treating the TMJ dysfunction is disclosed in U.S. Pat. No. 4,568,280; a craniomandibular appliance of a unitary insert of a remoldable thermoplastic material in the form of a dental arch is molded to the person's mouth in situ for positioning the mandible in a more forward position to obtain a reduced click or nonclick condylar position.

Another method of treatment for the TMJ disorders is disclosed in U.S. Pat. No. 4,671,766; a two-component intra-oral orthotic appliance with a wing on each component (where one fits in the maxillary arch and the other fits in the mandibular arch) is used to support the TMJ by closing the mouth so that the wing of each of the two components engages in a predetermined position to allow proper aligning of the TMJ for repair.

Yet another approach for protecting the TMJ is disclosed in U.S. Pat. No. 5,152,301 that discloses a thermoplastic mouthguard that has occlusal posterior pads on the bottom side of the base along the posterior portions of the guard to space apart the anterior teeth of the lower jaw from the anterior portion of the bottom side of the U-shaped base and to lessen pressure and possible impact forces exerted at the TMJ.

U.S. Pat. No. 4,810,192 is directed to a two stage intra-oral protective system for protecting teeth, lips, and jaw from injury and/or for supporting the TMJ in a relatively fixed position; the instant invention is an improvement over this device, since it provides greater protection of a larger area, the vital cranial triad which includes the TMJ, in only one stage and allows for audible speech, reduces sleep disorders of snoring, grinding and clenching of teeth with additional benefits.

SUMMARY OF THE INVENTION

The present invention is directed to a jaw-joint therapeutic and protective device for protecting a wearer's lips, tongue, teeth, VCT, and other oral structures within the full maxillary and mandibular arches of the mouth, and jaw-joint structures by repositioning the condyle in relationship to the fossae comprising:

a) a U-shaped base having a bilateral posterior dental region and an anterior dental region with integrated maxillary and mandibular components where the components are adapted for securement within the full maxillary and mandibular arches of the mouth, whereby the mandibular component is offset downwardly and forwardly from the maxillary component so that the mandible is set in a protruding position, b) an occlusal impact chamber in the mandibular and maxillary dental region of the base filled with a resilient material for absorption and dissipation of shock through the teeth and the device away from the jaw-joint and related facial structures.

c) the maxillary component comprising lingual, labial, and buccal walls projecting upwardly from the base forming with the base a maxillary channel for seating and protecting the maxillary teeth, and a reinforced anterior dental region with a labial flange, d) an articulating rim in the lingual wall of the maxillary component in the anterior dental region of the device that eliminates the need for a palatal component, so that the tongue of the wearer can be placed against the lingual surface of the anterior maxillary teeth for articulating speech, e) the mandibular component comprising lingual, labial, and buccal walls projecting downwardly from the base forming with the base a mandibular channel for seating and protecting the mandibular teeth, and a reinforced anterior lingual component with a deep labial flange to secure the mandibular arch to the downward and forward position, and f) a functional air-way passage in the anterior of the integrated components to facilitate breathing, expectorating and speaking, wherein the reinforced anterior and posterior dental regions of the maxillary and mandibular components are composed of a resilient thermoplastic material for dissipation and absorption of shock imposed upon the wearer's head during sport conditions, where the device in direct contact with the tooth surfaces is made of thermoplastic material that softens when heated above body temperature and rigidly stiffens when cooled so that the device can be perfectly fitted in situ, and remainder of the device is made of a rigid elastomeric material that maintains its rigidity at all times regardless of being heated in water above body temperature.

The present invention also relates to a method of fitting in situ by the wearer of the above mentioned jaw-joint protective device comprising heating the device in hot water to a temperature greater than body temperature to soften certain portions of the device and immediately placing it in the wearer's mouth and the wearer biting down on the base so as to make teeth impressions in the base and then cooling the device whereby the device harden to a rigid form maintaining the impression of the teeth and arch form of the wearer thereby customizing the device.

BRIEF DESCRIPTION OF THE DRAWINGS

FIG. 1 is a partial side view of the head showing the components of the functional change in the temporomandibular joint complex with the jaw-joint protective device in place.

FIG. 2 is a sectional frontal view of the mouth showing the airway opening or expectorant orifice in the jaw-joint protective device and no palatal component.

FIG. 3 is a frontal view of the protective device.

FIG. 4 is a side view of the protective device.

FIG. 5 is a top plan view of the device.

FIG. 6 is a view looking from the rear to the front of the device.

DETAILED DESCRIPTION OF THE INVENTION

It has been found that a jaw-joint protective device composed of two different types of materials for different purposes can be used by a wearer to provide protection not only to the oral cavity but also to the vital cranial triad (VCT) and component structures. The VCT broadens the defined structural component of what is commonly known as the temporomandibular joint. The invention supports the mandible and condyle in a relatively fixed position thereby stabilizing the jaw and VCT during head contact activities and/or to permit the components of any VCT disorders to be realigned reducing load forces to the jaw-joint during head contact and/or physical activities or bodily jarring forces.

This device is simple in structure but it is strong in purpose for achieving the maximum protection for the delicate bones and structures of the base of the skull, the jaw-joint and oral cavity. The simple jaw-joint protective device of the present invention does not need custom fitting but can be simply adapted to a wearer's mouth perfectly in situ by the wearer heating the device in water and then placing it in his/her mouth and biting down on the device so as to make an impression of the occlusal surfaces of the teeth in the occlusal impact surface of the dental arches of the device which will set up in a few seconds.

In order to understand and appreciate the structural features and benefits of the jaw joint protective device of the present invention, a brief review of the anatomy for which the device protects will be described.

FIG. 1 shows the functionally protected position of the VCT complex with the device in place. The areas of the head, protected by the device are the oral cavity or mouth that is composed of the teeth that sits in a rigidly fixed upper jaw and a moveable lower jaw which is movably connected to the cranium at the temporomandibular joint (TMJ). The joint is defined by two primary bones, the mandibular bone 1, which articulates with the temporal bone as a ball (condyle 2) and socket (glenoid fossa 3) joint.

Referring to either side of the human head, the temporal bone houses the very thin and delicate glenoid fossa 3 (lying above this fossa is the brain) the socket of the temporomandibular joint. The articular eminence 5 forms the anterior component of the fossa. Positioned between the condyle 2, the most posterior ball-like structure of the mandible, and the fossa 3 is the meniscus 4 (cartilage or disc) of the TMJ. The auditory meatus 6, temporal tympanic bones 7 a, b,.c, and post glenoid process 8 are also shown. The post glenoid process 8 and the anterior superior surface of the temporal tymanic bone unite at 9. Housed in the temporal tympanic bone are the auditory and balance mechanisms, among other vital structures. Medially and inferiorly to the medial surface of the condyle is the inferior surface of the petrous temporal bone porting a complex of cranial nerves trunks as they exit from the base of the brain and housing the internal carotid artery which is the primary supply of blood to the brain.

In the case of internal derangement including sports related injuries of the VCT, the forces from head, jaw or facial blows abruptly slams the condyle against the delicate structures of the vital cranial triad. These load forces will produce radiographically discernible fractures of the delicate bones and contusions, compressions, or herniations of the soft tissue of the VCT. Thus, it should come as no surprise that athletes with VCT injuries often present symptoms reflecting neurologic and circulatory deficit. These symptoms include headache, earache, facial pain, bloodshot eyes, photosensitivity, muscle weakness, pain and numbness of extremities, vomiting, vertigo, impaired speech, raspy voices, and decrease in hearing abilities among other clinical symptoms.

In conjunction with the aforementioned structures, the mandibular and maxillary dentition and gingiva, as well as, the tongue, lip, and other oral structures must be protected during sports activities.

In accordance with the present invention, the device (FIGS. 3 and 4) employs a design to overcome dental and jaw-joint problems typically as a result of contact sports. The device is composed of a reinforced anterior dental region and bilateral posterior dental regions where the maxillary (mx) and mandibular (md) teeth are functionally seated having labial border 10*mx* and 10*md*, lingual border 15, buccal border 11*mx* and 11*md*, articular rim 12, and lingual lock 13. The jaw joint protector repositions the lower jaw and condyle in a downward and forward position relative to the normal or centric position of the condyle. In other words, the lower jaw is extended in a prognathic position. This device also establishes an occlusal offset that positions the incisal surfaces of the mandibular incisal teeth downward and forward in relationship to the maxillary incisal teeth. This device also establishes an occlusal lock that creates a relationship between the upper and lower teeth in such a way as to minimize lateral, adverse, and relative movement during contact. In other words, the device maximizes jaw stability and locks the lower jaw in an extended position. The downward and forward position of the lower jaw in conjunction with the device creates the anterior functional free-way space and force attenuation space of the jaw-Joint.

A palatal portion commonly found in conventional mouthpieces normally ending just before the soft palate of the mouth is absent from this jaw joint protective device because of the engineered design for strength in the mandibular and maxillary components of this device; moreover, it would impair articulated speech and in many cases elicited a gag reflex. The labial-buccal borders are present and positioned in the mucco-buccal fold of the mouth avoiding impingement of the labial frennum and posterior muscle attachments.

FIG. 5 shows that the lingual surface is reinforced by the articular rim behind the maxillary anterior teeth from canine to canine; likewise, the lingual mandibular flange area is reinforced by the deep mandibular lock in the anterior from canine to canine.

When the device is placed in the mouth with the mandible placed in a functionally protruded position, the mandibular and maxillary units being integrated into one unit protects the oral cavity and positions the condyle of the VCT into a protective and exaggerated position that also promotes healing. The engineered mandibular jaw placement is governed by the device, the kinesiological functional physiology, the condyle-fossa physiology, the force attenuation space, and the functional free-way space.

FIGS. 1 and 2 show that the design of the jaw joint protective device is such that the upper and lower dental arches are held in a spaced-apart position of desired dimensions with an airway 14 (or saliva orifice) so that the participant wearing the device can readily breathe or expectorate or talk, depending on the activity. The anterior airway space 14 can be used as a means to grasp, which enables the jaw joint protective appliance to be removed from an injured or unconscious participant.

FIG. 6 shows the lingual view of the maxillary arch that has a thickened, tapered, depressed portion in the anterior region that defines an articulating rim 12 which aids in the production of speech and gives support to the lingual surface of the anterior teeth. This articulating rim combined with the anterior free way air space 14 enables the wearer to speak, to breathe actively and passively through the mouth while wearing the jaw-joint protective appliance.

The present invention also relates to a method of fitting in situ by the wearer of the above mentioned jaw joint protective device. Either the user or someone assisting him, for instance in the case of a minor child, can heat the device in hot water to a temperature greater than body temperature but less than or equal to 100° C. to soften certain portions of the device, as engineered, and immediately placing it in the wearer's mouth. The wearer then bites down on the base so as to make teeth impressions in the base and applies suction and pressure with, e.g., the tongue, fingers lips, lips, oral muscular, to create a good firm fit. Then the device is removed from the mouth and cooled down whereby the device harden to a rigid form. The cooling step only takes a few seconds. This device is mass produced in various sizes to fit different prospective users such as men, women, and children. It can be produced, for example, by injection molding techniques that are well known in the art.

The occulsal bite channel of the device is normally made of a heavy duty plastic material such as ethylene vinyl acetate that can withstand pressure, is easily molded, and is inert to the mouth chemistry of the person (or participant) wearing it. This plastic material must be able to soften when heated above body temperature but below or equal to 100° C. and yet to harden again when it is cooled down for molding in a wearer's mouth. Body temperature when measured in the mouth is about 37° C. Many materials can either be designed to meet this requirement of softening and hardening or already exist in the plastic industry. Natural rubber can also be used for producing the jaw-joint protector of the present invention which rubber must be heavy duty, non-toxic, and inert which would be well known to a person in this art.

The resilient material that is used as the primary foundation for the framework and shape for the reinforced anterior dental region in the maxillary and mandibular components and posterior component bilaterally would normally be prepared from a different material from that of the rest of the device that serves the function of strength for protection. The material is normally a thermoplastic material such as an elastomer. An examples of this elastomer is a Kraton material. Natural rubber can also be used for producing these resilient portions of the jaw-joint protector of the present invention which rubber must be heavy duty, non-toxic, and inert which would be well known to a person in this art. Other materials for the device that meet the specifications of the American Dental Association for intra-oral use would be known to a person in the art.

Many advantages of the jaw-joint protective device of the present invention exist over the conventional mouth guards. The present invention absorbs shock to the head, displaces the condyle in a downward and forward position creating the force attenuation space dissipating the shock forces to the VCT, and protects maxillary and mandibular dentition. This jaw-joint protector also eliminates compression of the disc and condyle-fossa space of the TMJ with trauma to the head, provides greater stability against traumatic displacement of the lower jaw onto the delicate bones in the head, decreases trauma to the anterior components of the tongue, and decreases the incident of lip injuries "the tooth through the lip syndrome".

The continued wearing of this device of the present invention promotes healing of an injured condyle-fossa complex and other facial structures while the athlete participates actively in sports or is at rest. Since articulated speech can be performed and nutrients passed through the air way space when the device is being worn by a person and is comfortable in the mouth, it is conceivable that this device can be used in arch stabilization and repair of other facial and jaw fractures; therefore, user of the device can use the device as a medical device. In other words, the jaw-joint protector of the present invention facilitates remodeling and repair of injured condyle-fossa relationship, VCT components and other facial bones. This device also increases functional physical output and strength of the athlete by repositioning the condyle away from the injured structures in the VCT; this is another incentive why it can be worn either while a wearer is actively participating in a sport or just performing normal everyday activities or being at rest. This device can also be used to increase palatal air flow and patterns during sleep and thereby reduce snoring. The wearing of this device will also reduce clenching and grinding of the teeth during sleep.

In summary, the continued use of the jaw joint protector of the present invention provides increased safety while actively engaging in sports that can produce trauma to the head.

What is claimed:

1. A jaw joint therapeutic and protective device composed of a first and a second material for protecting a wearer's lip, teeth, and other delicate structures of the head including the vital cranial triad (VCT), which is comprised of the bones and tissue structure found in the temporomandibular joint, temporal tympanic bone, and the inferior surface of the petrous temporal bone and related structures within the full maxillary and mandibular arches of the mouth, comprising a) a U-shaped base having a bilateral posterior dental region and a reinforced anterior dental region with integrated maxillary and mandibular components where the components are adapted for securement within the full maxillary and mandibular arches of the mouth, where the mandibular component is offset downwardly and forwardly from the maxillary component so that the mandible is set in a protruding position, b) a full arch occlusal impact chamber in the maxillary and mandibular components of the base filled with the first material which is a hard resilient material for dissipation and absorption of shock imposed upon the mandible, maxilla, head and facial structures, and the second material used for remainder of the device that is a thermoplastic material that softens when heated to a temperature greater than body temperature but less than or equal to 100° C. and rigidly stiffens when cooled so that the device can be perfectly fitted in situ, c) the maxillary component comprising lingual, labial and buccal walls projecting upwardly from the base forming with the base a maxillary channel for seating and protecting the maxillary teeth, and the reinforced anterior dental region with a labial flange, d) an articulating rim in the lingual wall of the maxillary component in the anterior dental region of the device to support the maxillary anterior teeth, and permitting the tongue of the wearer to be placed against the lingual surface of the anterior maxillary teeth for articulating speech, e) the mandibular component comprising lingual, labial, and buccal walls projecting downwardly and forwardly from the base forming with the base a mandibular channel for seating and protecting the mandibular teeth, and the reinforced anterior mandibular dental region with a deep labial flange to support and guide the mandible such that the mandible is in an engineered functionally prognathic position creating a force attenuating recoil space of the jaw-joint, and f) a functional air passageway from canine to canine in the anterior of the integrated components to facilitate breathing and speech, wherein the reinforced anterior dental regions of the maxillary and mandibular components and the posterior components bilaterally maintains the framework and shape of the device and dissipates and absorbs shock imposed upon the wearer's head.

2. The device of claim 1 wherein the hard resilient material is a thermoplastic elastomer.

3. The device of claim 1 wherein the functional passage is an airway or expectorant orifice.

4. The device of claim 1 wherein impressions made in the anterior components of the base of the device supported by the the articulating rim of the maxillary arch and the reinforced anterior dental region with the deep labial flange of the mandibular arch creates incisal locks even though the articulating rim is diminished in size but maintain the stability of the lock, while the incisal locks maintain the stability and strength for the incisal teeth but the articulating rim is reduced to insure tongue posture against the lingual surface of the anterior teeth to promote articulation and speech with the jaw-joint therapeutic and protective device in place.

5. The device in claim 1 wherein the hard resilient and thermoplastic materials of the device will maintain the mandibular and maxillary dental arches locked in a bite surface that stabilizes the jaw against lateral and traumatic jaw displacement which maintain the mandibular prognathic repositioning of the lower jaw and integrity of the device during the boil and bite phase of fitting.

6. The device of claim 1 wherein the functional air passageway creates a greater air flow than in conventional mouthguards and active airflow and freeway space for articulation and eliminating the need for the palatal component of the conventional mouthguard.

7. A method of treating a jaw-joint disorder and other facial fractures in a person having such a disorder comprising wearing the device of claim 1 by a person when participating in athletic activity or when in need to correct such disorder whereby the temporomandibular joint and jaw components are held stable and in their functional position for a sufficient time period in order to afford protection and healing thereof.

8. A method of fitting in situ the device of claim 1 in the mouth of a user comprising heating the device in hot water to a temperature greater than body temperature but less than or equal to 100° C. to soften certain portions of the device and immediately placing it in the wearer's mouth and the wearer biting down on the base so as to make teeth impressions in the base and applying suction and pressure with the tongue, lips, and oral musculature and then cooling the device down whereby the device hardens to a rigid form.

9. A method of treating sleep-disorders such as snoring, grinding and clenching of teeth comprising wearing the device of claim 1 by a person suffering with such disorder when sleeping.

* * * * *